US007622256B2

(12) United States Patent
Johnson et al.

(10) Patent No.: US 7,622,256 B2
(45) Date of Patent: Nov. 24, 2009

(54) METHOD FOR SELECTING COMPOUNDS THAT MODULATE MIF-INDUCED EXPRESSION OF ICAM-1 AND/OR VCAM-1

(75) Inventors: Kirk W. Johnson, Alameda, CA (US); Sharmila Vijay, Alameda, CA (US); Matthew Gross, Alameda, CA (US); Federico C. A. Gaeta, Mountain View, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 11/807,604

(22) Filed: May 29, 2007

(65) Prior Publication Data
US 2007/0281966 A1 Dec. 6, 2007

Related U.S. Application Data

(60) Provisional application No. 60/810,034, filed on May 31, 2006, provisional application No. 60/812,338, filed on Jun. 8, 2006.

(51) Int. Cl.
*C12Q 1/68* (2006.01)
*G01N 33/53* (2006.01)
(52) U.S. Cl. ............................ 435/6; 435/7.1; 435/7.21; 436/501
(58) Field of Classification Search ........................ None
See application file for complete search history.

(56) References Cited

U.S. PATENT DOCUMENTS

| 2003/0195194 A1 | 10/2003 | Gaeta et al. |
| 2006/0008446 A1 | 1/2006 | Watkins |
| 2006/0160843 A1 | 7/2006 | Johnson et al. |
| 2007/0072899 A1 | 3/2007 | Johnson et al. |
| 2008/0114027 A1 | 5/2008 | Johnson et al. |
| 2008/0181876 A1 | 7/2008 | Johnson et al. |

FOREIGN PATENT DOCUMENTS

| WO | WO 99/64037 A1 | 12/1999 |
| WO | WO 01/05422 A2 | 1/2001 |
| WO | WO 03/104178 A | 12/2003 |
| WO | WO 03/104203 A | 12/2003 |
| WO | WO 2004/058713 A | 7/2004 |
| WO | WO 2005/058304 A | 6/2005 |
| WO | WO 2006/045505 A | 5/2006 |
| WO | WO 2006/063048 A2 | 6/2006 |
| WO | WO 2006/108671 A | 10/2006 |
| WO | WO 2007/047978 A2 | 4/2007 |

OTHER PUBLICATIONS

Ledeboer et al. (2007). The glial modulatory drug AV411 attenuates mechanical allodynia in rat models of neuropathic pain. Neuron Glia Biology. 2:279-291.*
Bloom & Bennett, "Mechanism of a reaction in vitro associated with delayed-type hypersensitivity," Science 153:80-82 (1966).

Calandra & Roger, "Macrophage migration inhibitory factor: a regulator of innate immunity," Nat Rev Immunol 3:791-800 (2003).
Calandra, et al., "Protection from septic shock by neutralization of macrophage migration inhibitory factor," Nat Med 6:164-170 (2000).
Feng, et al., "Ibudilast, A Nonselective Phosphodiesterase Inhibitor, Regulates Th l/Th2 Balance And NKT Cell Subset In Multiple Sclerosis," Mult Scler 10:494-498 (2004).
Fujimoto, et al., "Ibudilast, A Phosphodiesterase Inhibitor, Ameliorates Experimental Autoimmune Encephalomyelitis In Dark August Rat," J Neuroimmunology 95:35-42 (1999).
Futaki, "Treatment of Meniere's Disease Comparison of Prednisolone and Ketas," Practica Otologica Kyoto 83(9):1463-1471 (1990) English Abstract.
Gibson, et al., "The Inhibitory Profile of Ibudilast Against the Human Phosphodiesterase Enzyme Family," Eur J Pharmacology 538:39-42 (2006).
Gul, et al., "The interaction Between IL-1β and morphine: Possible Mechanism of the Deficiency of Morphine Induced Analgesia in Diabetic Mice," Pain 89:39-45 (2000).
Itoh, et al., "A Therapeutic Strategy To Prevent Morphine Dependence And Tolerance By Coadministration Of Camp-Related Reagents With Morphine," Methods and Findings in Experimental and Clinical Pharmacology 20(7):619-625 (1998).
Johnston, et al., "A Role for Proinflammatory Cytokines and Fractalkine in Analgesia, Tolerence and Subsequent Pain Felicitation Induced by Chronic Intrathecal Morphine," J Neurosci 24:7353-7365 (2004).
Kawanokuchi, et al., "Effects Of Interferon-Beta on Microglial Functions As Inflammatory And Antigen Presenting Cells In The Central Nervous System," Neuropharmacology 46:734-742 (2004).
Koda, et al., "Up-Regulation Of Macrophage Migration-Inhibitory Factor Expression After Compression-Induced Spinal Cord Injury In Rats," Acta Neuropathol 108:31-36 (2004).
Mamiya, et al., "Involvement of Cyclic AMP Systems in Morphine Physical Dependence in Mice: Prevention of Development of Morphine Dependence by Rolipram, A Phosphodiesterase 4 Inhibitor," Br J Pharmacol 132(5):1111-1117 (2001).
Mizuno, et al., "Neuroprotective Role Of Phosphodiesterase Inhibitor Ibudilast On Neuronal Cell Death Induced By Activated Microglia," Neuropharmacology 46:404-411 (2004).
Nabeshima, et al., "Drug Dependence Formation Inhibitor: Comprising Phosphodesterase Inhibitor, Preferably Rolipram, Especially for Combatting Narcotic Anaslgesic Dependence," Database WPI, Derwent Publications, Ltd., London, GB p. 7, AN 1997-506303 (1997).
Narita, et al., "Role Of Astrocytes in Rewarding Effects Of Drugs Of Abuse," Jpn J Neuropsychopharmacol 26:33-39 (2006) English Abstract.

(Continued)

Primary Examiner—Christine J Saoud
Assistant Examiner—Jon M Lockard
(74) Attorney, Agent, or Firm—Robins & Pasternak LLP

(57) ABSTRACT

Methods of antagonizing MIF activity using ibudilast are described. Also described are methods of screening for MIF antagonists. These agents can be used for treating addictions, including drug and behavioral addictions, as well as for treating neuropathic pain.

1 Claim, No Drawings

OTHER PUBLICATIONS

Narita, et al., "Direct Evidence of Astrocytic Modulation in the Development of Rewarding Efects Induced by Drugs of Abuse," *Neuropsychopharmacology* 31:2476-2488(2006).

Narita, et al., "Comparatice Pharmacological Profiles of Morphine and Oxycodone Under a Neuropathic Pain-Like State in Mice: Evidence for Less Sensitivity to Morphine," *Nature Neuropsychopharmacolog* 1-16 (2007) *Online Article*.

Obernolte, et al., "The cDNA of a Human Lymphocytic Cyclic-AMP Phosphodiesterase (PDE IV) Reveals a Multigene Family," *Gene* 129:239-247 (1993).

Raghavendra, et al., "The Role of Spinal Neuroimmune Activation in Morphine Tolerence/Hyperalgesia in Neuropathic and Sham-Operated Rats," *J Neurosci* 22(22):9980-9989 (2002).

Raghavendra, et al., "Attenuation of Morphine Tolerence, Withdrawal-Induced Hyperalgesia and Associated Spinal Inflammatory Immune Responses by Propentofylline in Rats," *Neuropsychopharmacology* 29(2):327-334 (2004).

Rile, et al., "Potentiation of Ibudilast Inhibition of Platelet Aggregation of Endothelial Cells," *Thrombosis Research* 102:239-246 (2001).

Santos & Morand, "The Role Of Macrophage Migration Inhibitory Factor In The Inflammatory Immune Response And Rheumatoid Arthritis," *Wein Med Wochenschr* 156:11-18 (2006).

Shavit, et al., "Interleukin-1 ANtogonizes Morphine Analgesia and Underlies Morphine Tolerance," *Pain* 115:50-59 (2005).

Song, et al., "The Involvement of Glial Cells in the Development of Morphine Tolerance," *Neurosci Res* 39:281-286 (2001).

Souness, et al., "Possible Role of Cyclic AMP Phosphdiesterases in the Actions of Ibudilast on Eosinophil Thrmbaxane Generation and Airways Smooth Muscletone," *Br J Pharmacol* 111:1081-1088 (1994).

Sugiyama, et al., "SPECT Evaluation of Effect of Cerebral Vasodilator by the Subtraction Method Using Tc-99m HMPAO," *No To Shinkei* 45(2):139-142 (1993) *English Abstract*.

Suzumura, et al., "Ibudilast Suppresses Tnfalpha Production By Glial Cells Functioning Mainly As Type III Phosphodiesterase Inhibitor In The CNS," *Brain Res* 837:203-212 (1999).

Takuma, et al., Ibudilast Attenuates Astrocyte Apoptosis Via Cyclic GMP Signalling Pathway in an In Vitro Reperfusion Model, *Br J Pharmacology* 133:841-848 (2001).

Tsuru, et al., "Preference Test of 3-Isobutyryl-2-Isopopylpyrazolo [1,56-a] Pyradine (KC-404) On Rats," *Pharmacometrics* 36(6):449-457 (1988) *English Abstract*.

Wakita, et al., "Ibudilast Phosphodiesterase Inhibitor, Protects Against White Matter Damage Under Chronic Cerebral Hyperfusion in the Rat," *Brain Res* 992:53-59 (2003).

Watkins, et al., "Glia: Novel Counter-Regulators Of Opoid Analgesia," *Trends in Neurosci* 28:661-669 (2005).

Watkins, et al., "Beyond Neurons : Evidence That Immune and Glial Cells Contribute to Pathological Pain States," *Physiol Rev* 82:981-1011 (2002).

Watkins, et al., "Targeting Glia to Control Clinical Pain: An Idea Whose Time has Come," *Drug Disc Today* 1(1):83-88 (2004).

Bender, et al., "Cyclic Nucleotide Phosphodiesterases: Molecular Regulation To Clinical Use," *Pharmacol Rev* 58:488-520 (2006).

Castro, et al., "Cyclic Nucleotide Phosphodiesterases And Their Role In Immunomodulatory Responses: Advances In The Development Of Specific Phosphdiesterase Inhibitors," *Medicinal Res Rev* 25(2):229-244 (2005).

He, et al., "Novel Cyclic Compounds As Potent Phosphdiesterase 4 Inhibitors," *J Med Chem* 41:4216-4223 (1998).

Huang, et al., "Preferential Inhibition Of Human Phosphodiesterase 4 By Ibudilast," *Life Sci* 78:2663-2668 (2006).

Johnson, et al., "72 AV411: A Unique, Orally Active Glial Inhibitor For Neuropathic Pain," *Eur J Pain* 10(1):S21 (2006).

Kiritsy-Roy, et al., "Dopamine D-1 And D-2 Receptor Antagonists Potentiate Analgesic And Motor Effects Of Morphine," *Pharmacol Biochem Behav* 32:717-721 (1989).

Ledeboer, et al., "Ibudilast (AV-411). A New Class Therapeutic Candidate For Neuropathic Pain And Opoid Withdrawal Syndromes," *Exp Opin Invest Drugs* 16(7):935-950 (2007).

Miguel-Hidalgo, "Withdrawal From Free-Choice Ethanol Consumption Results In Increased Packing Density Of Glutamine Synthetase-Immunoreactive Astrocytes In The Prelimbic Cortex Of Alcohol-Preferring Rats," *Alcohol* 41:379-385 (2006).

Suzumura, et al., "Ibudilast Suppresses TNFα Production by Glial Cells Functioning Mainly as Type III Phosphodiesterase Inhibitor in the CNS," *Brain Res* 837:203-212 (1999).

Tsuneichi, et al., "Effect Of Continuous Oral Administration Of KC-764 On Monoamines, Acetylcholine And Neuroactive Amino Acids Contents In Rat Brain," *Clinical Rep* 28(8):113-119 (1994) *Original Japanese Article And English Abstract*.

Kudo, et al., "General Pharmacological Activity Of KC-404—Effect On Central Nervous System," *Kiso to Rinsho* 19(11):5476-5484 (1985) *Original Japanese Article With Attached Certified English Translation*.

Hutchinson, et al., "Opoid-Induced Glial Activation: Mechanisms of Activation and Implications for Opoid Analgesia, Dependence, and Reward," *Sci World J* 7(S2):98-111 (2007).

Park, et al., "The Effects Of Ibudilast On Diabetic Peripheral Neuropathy," *Jpn Pharmacol Ther* 19(5):337-341 (1991) *English Translation, Original Japanese Article, And English Abstract*.

Park, "The Effects Of Ibudilast On Diabetic Peripheral Neuropathy, Part 2" *Jpn Pharmacol Ther* 23(6):133-139 (1995) *English Translation, Original Japanese Article, And English Abstract*.

Shimomura, et al., "Analgesic Induced Headaches: Succesful Treatment With Ibudilast," *Geriatr Med* 29(2):315-323 (1991) *Original Japanese Only*.

Shimomura, et al., "Analgesic-Induced Headaches: Succesful Treatment With Ibudilast," *Headache* 31:483 (1991).

Souness, et al., "Potential Of Phosphodiesterase Type 4 Inhibitors In The Treatment Of Rheumatoid Arthritis," *Curr Res Rheum Arthritis* 2(6):255-268 (1998).

Yamauchi, "Effects Of Ibudilast On Diabetic Neuropathy. Subjective And Objective Improvement By Ibudilast," *Clin Res* 71(9):262-272 (1994) *English Translation and Original Japanese Article*.

Yasaki, et al., "Effect Of Ibudilast On Experimental Diabetic Neuropathy," *J Japan Diab Soc* 37(3):215-222 (1994) *English Translation, Original Japanese Article, and English Abstract*.

\* cited by examiner

METHOD FOR SELECTING COMPOUNDS THAT MODULATE MIF-INDUCED EXPRESSION OF ICAM-1 AND/OR VCAM-1

CROSS-REFERENCE TO RELATED APPLICATIONS

This application claims the benefit under 35 U.S.C. §119 (e)(1) of provisional application 60/810,034, filed May 31, 2006 and provisional application 60/812,338, filed Jun. 8, 2006, which applications are hereby incorporated by reference in their entireties.

FIELD OF THE INVENTION

The present invention relates generally to activity exhibited by ibudilast (also termed "AV411"). In particular, the present invention pertains to methods for antagonizing macrophage migration inhibitory factor (MIF) activity using ibudilast. The invention also relates to methods for identifying agents for treating and/or preventing neuropathic pain, methods for identifying agents useful for opiate withdrawal and for treating other addictions and dependence, as well as methods for identifying agents useful for treating and/or preventing other disorders wherein MIF activity and/or glial activation are implicated.

BACKGROUND OF THE INVENTION

The small molecule, ibudilast, (3-isobutyryl-2-isopropylpyrazolo[1,5-a]pyridine), is a non-selective inhibitor of cyclic nucleotide phosphodiesterase (PDE) (Fujimoto et al., (1999) J. of Neuroimmunology 95:35-92). Ibudilast displays glial attenuating properties, differentiating it from some other PDE inhibitors (Suzumuar et al., Brian Res. (1999) 837:203-212). Glial cell activation may have multiple, diverse neurological consequences including contributions to neuropathic pain, opiate withdrawal/addiction and Alzheimer's (Narita et al., Nihon Shinkei Seishin Yakurigaku Zasshi (2006) 26:33-39). Ibudilast also acts as an LTD4 antagonist, an anti-inflammatory, a PAF antagonist, and a vasodilatatory agent (Thompson Current Drug Reports). Ibudilast is thought to exert a neuroprotective role in the central nervous system of mammals, presumably via suppression of the activation of glial cells (Mizuno et al., (2004) Neuropharmacology 46: 404-411).

Ibudilast has been widely used in Japan for relieving symptoms associated with ischemic stroke or bronchial asthma. Marketed indications for ibudilast in Japan include its use as a vasodilator, for treating allergy, eye tissue regeneration, ocular disease, and treatment of allergic ophthalmic disease (Thompson Current Drug Reports). In recent clinical trials, its use in the treatment of multiple sclerosis, an inflammatory disease of the central nervous system, has been explored (News. Medical. Net; Pharmaceutical News, 2 Aug. 2005).

The cytokine macrophage migration inhibitory factor (MIF) has been shown to play a role in multiple inflammatory processes, primarily by influencing macrophage function (Bloom and Bennett, Science (1966) 153:80; and Calandra and Roger, Nat. Rev. Immunol. (2003) 3:791-800). Neutralizing antibodies to MIF have been demonstrated to be effective therapeutics in preclinical models of rheumatoid arthritis, endotoxemia and septic shock (Calandra et al., Nat. Med. (2000) 6:164-170; and Santos and Morand, Wein. Med. Wochenschr. (2000) 156:11-18). MIF mRNA is upregulated in microglia three days post-spinal cord injury and may act as a modulator to inflammatory cytokines (Koda et al., Acta Neuropathol. (2004) 108:31-36).

While the use of ibudilast for a number of varying indications, including the regulation of mononuclear and glial cell response (Kawanokuchi et al., Neuropharmacology (2004) 46:734-742; Feng et al., Mult. Scler. (2004) 10:494-498) has been reported to date, to the best of applicants' knowledge, its activity as an inhibitor of the cytokine macrophage migration inhibitory factor (MIF) has heretofore remained unexplored.

There remains a need for identifying improved compounds and compositions that inhibit MIF.

SUMMARY OF THE INVENTION

The present invention is based on the discovery that ibudilast acts as an antagonist of MIF activity. As glial cells (astrocytes, microglia, oligodendrocytes) have cell-type functional similarities to monocytes/macrophages, MIF may influence glial cell activity. Therefore, antagonism of MIF binding to or activity on blood mononuclear and/or glial cells may account for its anti-inflammatory activity, as well as for the beneficial properties it exerts in neurological and other disorders. The glial attenuating activity displayed by ibudilast may be central to the mechanism for this small molecule's efficacy in neuropathic pain and opiate withdrawal and dependence syndromes. (See, U.S. Patent Publication No. 2006/0160843 for a description of the use of ibudilast to treat neuropathic pain, incorporated herein by reference in its entirety; and U.S. Patent Publication No. 2007/0072899, for a description of the use of ibudilast to treat opiate withdrawal and other dependence syndromes, incorporated herein by reference in its entirety).

These findings not only provide a potential molecular mechanistic link to ibudilast's pharmacological activities, but also provide evidence that other selective MIF antagonists may represent a new therapeutic approach for the treatment of neuropathic pain, opiate withdrawal and dependence, and for the treatment of other disorders where MIF activity and/or glial activation are implicated. In addition, there are diagnostic implications related to MIF binding and MIF antagonism.

In one aspect, then, the invention provides a method for attenuating MIF activity in a vertebrate subject. In certain aspects, MIF activity is inhibited by providing ibudilast.

In certain embodiments, the subject is a human. In certain embodiments, ibudilast is administered systemically, for example, via intravenous, subcutaneous, oral, intranasal, sublingual or other systemic routes. In other embodiments, ibudilast is administered centrally, for example, intrathecally. In certain embodiments, multiple therapeutically effective doses of ibudilast are administered to the subject. In certain embodiments, ibudilast is administered according to a daily dosing regimen. In certain embodiments ibudilast is administered twice a day. In certain embodiments, ibudilast is administered intermittently.

In additional embodiments, the invention is directed to a method for identifying a compound that modulates neuropathic pain. In certain embodiments, the method comprises screening a compound library to identify a small molecule that inhibits neuropathic pain.

In further embodiments, the invention is directed to a method of selecting a compound useful for treating neuropathic pain. The method comprises:

(a) exposing a peripheral blood mononuclear (PBMC) cell culture to a putative compound for treating neuropathic pain;

(b) providing MIF to the exposed cells in an amount and under conditions that normally provide for expression of intracellular adhesion molecule-1 (ICAM-1) and/or vascular cell adhesion molecule-1 (VCAM-1);

(c) comparing expression of ICAM-1 and/or VCAM-1 by the cells in step (b), to expression of ICAM-1 and/or VCAM-1 in a PBMC cell culture treated with MIF as in step (b) in the absence of the putative compound for treating neuropathic pain; and (d) selecting a compound from step (c) that inhibits expression of ICAM-1 and/or VCAM-1 relative to expression of ICAM-1 and/or VCAM-1 in the absence of the compound.

In certain embodiments, the above method further comprises testing the compound selected in step (d) in an acceptable model of neuropathic pain.

In additional embodiments, the neuropathic pain is selected from postherpetic neuralgia, trigeminal neuralgia, neuropathic pain associated with herpes, HIV, traumatic nerve injury, stroke, post-ischemia, fibromyalgia, reflex sympathetic dystrophy, complex regional pain syndrome, spinal cord injury, sciatica, phantom limb pain, multiple sclerosis, or cancer chemotherapeutic-induced neuropathic pain.

In other embodiments, the invention is directed to a method for identifying a compound that is useful for treating addictions, such as drug or behavioral addictions. In certain embodiments, the method comprises screening a compound library to identify a small molecule that is useful for treating addictions.

In additional embodiments, the invention is directed to a method of selecting a compound useful for treating addiction. The method comprises:

(a) exposing a peripheral blood mononuclear (PBMC) cell culture to a putative compound for treating addiction;

(b) providing macrophage migration inhibitory factor (MIF) to the exposed cells in an amount and under conditions that normally provide for expression of intracellular adhesion molecule-1 (ICAM-1) and/or vascular cell adhesion molecule-1 (VCAM-1);

(c) comparing expression of ICAM-1 and/or VCAM-1 by the cells in step (b), to expression of ICAM-1 and/or VCAM-1 in a PBMC cell culture treated with MIF as in step (b) in the absence of the putative compound for treating addiction; and (d) selecting a compound from step (c) that inhibits expression of ICAM-1 and/or VCAM-1 relative to expression of ICAM-1 and/or VCAM-1 in the absence of the compound.

In certain embodiments, the method above further comprises testing the compound selected in step (d) in an acceptable model of addiction.

In additional embodiments, the addiction is a drug addiction. In certain embodiments, the drug addiction is selected from an opiate addiction, a cocaine addiction, an amphetamine addiction, a methamphetamine addiction, a cannabinoid addiction, an alcohol addiction, or a nicotine addiction.

In further embodiments, the addiction is a behavioral addiction. In certain embodiments, the behavioral addiction is selected from an eating addiction, a drinking addiction, a smoking addiction, a shopping addiction, a gambling addiction, a sex addiction, or a computer use addiction.

These and other embodiments of the subject invention will readily occur to those of skill in the art in view of the disclosure herein.

DETAILED DESCRIPTION OF THE INVENTION

The practice of the present invention will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); Remington: *The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

All publications, patents and patent applications cited herein, whether supra or infra, are hereby incorporated by reference in their entirety.

I. DEFINITIONS

In describing and claiming the present invention, the following terminology will be used in accordance with the definitions described below.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

The term "addiction" is defined herein as compulsively using a drug or performing a behavior repeatedly that increases extracellular dopamine concentrations in the nucleus accumbens. An addiction may be to a drug including, but are not limited to, psychostimulants, narcotic analgesics, alcohols and addictive alkaloids such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, such as barbiturates, chlordiazepoxide, and alcohols, such as ethanol, methanol, and isopropyl alcohol. The term addiction also includes behavioral addictions, for example, compulsive eating, drinking, smoking, shopping, gambling, sex, and computer use.

A subject suffering from an addiction experiences addiction-related behavior, cravings to use a substance in the case of a drug addiction or overwhelming urges to repeat a behavior in the case of a behavioral addiction, the inability to stop drug use or compulsive behavior in spite of undesired consequences (e.g., negative impacts on health, personal relationships, and finances, unemployment, or imprisonment), reward/incentive effects associated with dopamine release, and dependency, or any combination thereof.

Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal.

By "pathological pain" is meant any pain resulting from a pathology, such as from functional disturbances and/or pathological changes, lesions, burns and the like. One form of pathological pain is "neuropathic pain" which is pain thought to initially result from nerve damage but extended or exacerbated by other mechanisms including glial cell activation. Examples of pathological pain include, but are not limited to, thermal or mechanical hyperalgesia, thermal or mechanical allodynia, pain arising from irritable bowel or other internal organ disorders, endometriosis pain, low back pain, pain arising from infection, inflammation or trauma to peripheral nerves or the central nervous system, multiple sclerosis pain, entrapment pain, neuropathic pain associated with certain syndromes such as viral neuralgias (e.g., herpes, AIDS), diabetic neuropathy, phantom limb pain, stump/neuroma pain, post-ischemic pain (stroke), fibromyalgia, reflex sympathetic dystrophy (RSD), complex regional pain syndrome (CRPS), cancer pain, vertebral disk rupture, and trigeminal neuralgia, cancer-chemotherapy-induced neuropathic pain, among others.

By "peripheral blood mononuclear cells" or "PBMC" is meant a population of cells isolated from peripheral blood of a mammal, such as a human, using, e.g., density centrifugation. Generally, a PBMC population includes mostly lymphocytes and monocytes and lacks red blood cells and most polymorphonuclear leukocytes and granulocytes.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

The terms "subject", "individual" or "patient" are used interchangeably herein and refer to a vertebrate, preferably a mammal. Mammals include, but are not limited to, murines, rodents, simians, humans, farm animals, sport animals and pets.

The term "about", particularly in reference to a given quantity, is meant to encompass deviations of plus or minus five percent.

The terms "effective amount" or "pharmaceutically effective amount" of a composition or agent, as provided herein, refer to a nontoxic but sufficient amount of the composition to provide the desired response, such as to suppress MIF activity in a subject, and optionally, a corresponding therapeutic effect. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation.

By "therapeutically effective dose or amount" of ibudilast is intended an amount that, when ibudilast is administered as described herein, brings about a positive therapeutic response.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a previously unrecognized activity of ibudilast, the antagonism of MIF activity. As explained above, ibudilast also displays glial cell activation and is useful for treating neuropathic pain and addictive disorders. Based on the discoveries presented herein, it appears that MIF antagonism may contribute to the glial attenuating activity demonstrated by ibudilast. This activity may be central to the mechanism for ibudilast's efficacy in neuropathic pain and opiate withdrawal and dependence syndromes. Thus, other antagonists of MIF may also display similar activities. Accordingly, the present invention provides methods for identifying such antagonists.

Additionally, based on the fact that ibudilast antagonizes MIF activity, ibudilast may be useful for treating a large number of disorders where MIF activity is implicated. Thus, ibudilast can be provided in compositions, as described further below, to antagonize MIF activity in a vertebrate subject, such as a human, to treat a whole host of disorders associated with MIF. MIF antagonists other than ibudilast for treating such disorders, can also be discovered using the screening methods described herein and subsequently used in compositions for treating these MIF-associated disorders.

Such disorders include, but are not limited to, various inflammatory disorders such as rheumatoid arthritis (see, e.g., Onodera et al., *Arthritis. Rheum.* (2004) 50:1437-1447; Lubetsky et al., *J. Biol. Chem.* (2002) 277:24976-24982); filariasis (Maizels et al., *Int. J Parasitol.* (2001) 31:889-898); pancreatitis (Sakai et al., *Gastorenterol.* (2003) 124:725-736); dermal photoaging of human skin (Watanabe et al., *J. Biol. Chem.* (2004) 279:1676-1683); obesity (Dandona et al., *J. Clin. Endocrinol. Metab.* (2004) 89:5043-

5047); drug resistance in cancer treatment (Lin et al., *Oncol. Rep.* (2005) 13:983-988); diabetes (Cvetkovic et al., *Endocrinol.* (2005) 146:2942-2951); invasiveness/metastasis of cancer cells (Hagemann et al., *J. Immunol.* (2005) 175:1197-1205); Guillain-Barre syndrome (Micolette et al., *J. Neuroimmunol.* (2005) 168:168-174; severe sepsis (Al-Abed et al., *J Biol. Chem.* (2005) 280:36541-36544); asthma (Rossi et al., *J. Clin. Invest.* (1998) 101:2869-2874); Neuro-Behcet's Disease (NBD) and conventional-form multiple sclerosis (C-MS) ((Ninno et al., *J. Neurol Sci.* (2000) 179:127-131); spinal cord injury (Fujimoto, S., Hokkaido Igaku Zasshi. (1997) 72:409-430 and Koda et al., *Acta Neuropathol (Berl)*. (2004) 108:31-36); bladder inflammation (Meyer-Seigler et al., *J Interferon Cytokine Res.* (2004) 24:55-63); nephropathy (Kim et al., *Mol. Med.* (2000) 6:837-848): cutaneous lymphoproliferative diseases such as Sezary Syndrome and mycosis fungoides (Umbert et al., *Brit. J. Dermatol.* (1976) 95:475-480); allergic neuritis (Breborowicz et al., *Scand J Immunol.* (1981) 14:15-20); atopic dermatitis, tumor progression and neoplasia, cell proliferation and tumor progression and angiogenesis (Orita et al., *Curr. Pharm. Des.* (2002) 8:1297-1317); anemia caused by maleria (McDevitt et al., *J Exp Med.* (2006) 203:1185-1196); and colitis (Morand, E. F., *Intern Med J.* (2005) 35:419-426). MIF antagonists are also useful as tautomerase inhibitors (see, e.g., Orita et al., *Curr. Pharm. Des.* (2002) 8:1297-1317).

In order to further an understanding of the invention, a more detailed discussion is provided below regarding ibudilast, compositions including ibudilast and screening methods for finding agents useful for treating neuropathic pain and addictions.

Ibudilast

Ibudilast is a small molecule drug (molecular weight of 230.3) having the structure shown below.

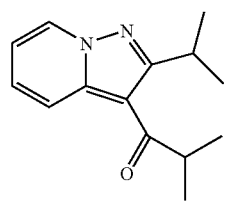

I

Ibudilast is also found under ChemBank ID 3227, CAS #50847-11-5, and Beilstein Handbook Reference No. 5-24-03-00396. Its molecular formula corresponds to $[C_{14}H_{18}N_2O]$. Ibudilast is also known by various chemical names which include 2-methyl-1-(2-(1-methylethyl)pyrazolo(1,5-a)pyridin-3-yl)1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and the brand name KETAS™. Ibudilast, as referred to herein, is meant to include any and all pharmaceutically acceptable salt forms thereof, prodrug forms (e.g., the corresponding ketal), and the like, as appropriate for use in its intended formulation for administration.

Ibudilast is a non-selective nucleotide phosphodiesterase (PDE) inhibitor (most active against PDE-3 and PDE-4), and has also been reported to have LTD4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca^{2+}$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9).

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), different physical forms (e.g., crystalline solids, amorphous solids), metabolites, and the like.

Screening Methods

One aspect of the invention provides methods of screening for compounds that modulate neuropathic pain. In other embodiments, the invention is directed to methods for identifying compounds useful for treating addictions, such as drug or behavioral addictions. In certain embodiments, the addiction is an opiate, cocaine, amphetamine, methamphetamine, cannabinoid, alcohol, or nicotine addiction. In other embodiments, the addiction is a behavioral addiction, for example, an eating, drinking, smoking, shopping, gambling, sex, or computer use addiction.

Molecules screened for the activities described above include but are not limited to small organic compounds, combinatorial libraries of organic compounds, nucleic acids, nucleic acid derivatives, saccharides or oligosaccharides, peptoids, soluble peptides, peptides tethered on a solid phase, peptides displayed on bacterial phage surface proteins, bacterial surface proteins or antibodies, and/or peptides containing non-peptide organic moieties.

For example, libraries of diverse molecular species can be made using combinatorial organic synthesis. See, e.g., Gordon et al. (1994) *J. Med. Chem.* 37:1335. Examples include but are not limited to pyrrolidines; oligocarbamates (Cho et al. (1993) *Science* 261:1303); peptoids such as N-substituted glycine polymers (Simon et al. (1992) *Proc. Natl. Acad. Sci. USA* 89:9367); and vinylogous polypeptides (Hagihara et al. (1992) *J. Am. Chem. Soc.* 114:6568).

A variety of approaches, known in the art, can be used to track the building blocks as they are added during synthesis so that the history of individual library members can be determined. These approaches include addressable location on a photolithographic chip (oligocarbamates), a deconvolution strategy in which "hits" are identified through recursive additions of monomers to partially synthesized libraries (peptoids, pyrrolidines, peptides) (Zuckermann et al. (1994) *J. Med. Chem.* 37:2678), and coding combinatorial libraries by the separate synthesis of nucleotides (Nielsen et al. (1993) *J. Am. Chem. Soc.* 115: 9812) or other organic moieties (Ohlmeyer et al. (1993) *Proc. Natl. Acad. Sci. USA* 90:10922) ("tags"). The coded tags associated with each library member can then be decoded after an agent has been selected. For example, nucleic acid tags can be decoded by DNA sequencing. Other methods for identifying active compounds in pools of small molecules include fractionating the pool by reverse phase HPLC or affinity selection/mass spectroscopy (Nedved et al., (1996) *Anal. Chem.* 68:4228).

Peptoid combinatorial libraries can also be used for identifying MIF antagonists. Peptoids are oligomers of N-substituted glycine (Simon et al. (1992) *Proc. Natl. Acad. Sci. USA* 89:9367) and can be used to generate chemically diverse libraries of novel molecules. The monomers may incorporate t-butyl-based side-chain and 9-fluorenyl-methoxy-carbonyl a-amine protection. The assembly of monomers into peptoid oligomers can be performed, for example, on a solid phase using the "submonomer method" of Zuckermann et al. (1992) *J. Am. Chem. Soc.* 114:10646. In this method, syntheses are conducted with Rink amide polystyrene resin (Rink et al. (1987) *Tetrahedron Lett.* 28:3787). Resin-bound amines are bromoacetylated by in situ activation of bromoacetic acid with diisopropyl-carbodiimide. Subsequently, the resin-bound bromoacetamides are displaced by addition of an amine. The amines may incorporate t-butyl-based protection of additional reactive groups. This two-step cycle is repeated until the desired number of monomers is added. The oligopeptide is then released from the resin by treatment with 95% trifluroacetic acid/5% water. The syntheses are performed, preferably, using a robotic synthesizer. See, e.g., Zuckermann et al. (1992) *Pept. protein Res.* 40:498; and Zuckermann et al. (1996) *Methods in Enzymology* 267:437. In the alternative, oligomerization of the peptoid monomers may be performed by in situ activation by either benzotriazol-1-yloxytris (pyrrolidino)phosphonium hexafluorphosphate or bromotris(pyrrolidino) phosphonium hexafluorophosphate. In this alternative method, the other steps are identical to conventional peptide synthesis using α-(9-fluorenyl methoxycarbonyl) amino acids (see, e.g., Simon et al. (1992), supra).

Compounds and libraries of compounds can be screened for their ability to antagonize MIF activity by treating peripheral blood mononuclear cells (PBMC) with a test compound or library of compounds as described above, and stimulating the cells with MIF. PBMCs for stimulation can be isolated from whole blood using techniques well known in the art, such as by using Ficoll-Hypaque density gradients. After centrifugation, adherent mononuclear cells can be, but need not be, separated from nonadherent mononuclear cells (NAMNC) by successive cycles of adherence to plastic for, e.g., 45 min. at 37 degrees C. In order to prepare stimulated cells, the therapeutic agent in question and PBMCs are combined. The amount of agent to be added will depend on the particular substance being tested. One of skill in the art can easily determine the appropriate concentration for use. MIF is then added approximately 30 minutes to 5 hours later, preferably about 45 minutes to 2 hours later, and more preferably about 1 hour after the test compound has been added. The plates are incubated for approximately 2-24 hours, or longer, after MIF is added, preferably 5 to 15 hours, and more preferably 7 to 10 hours, such as 9 hours.

The expression of intracellular adhesion molecule-1 (ICAM-1) and/or vascular cell adhesion molecule-1 (VCAM-1) are markers of MIF-stimulation. Thus, the expression of these molecules can be measured and compared to expression using MIF alone, without the test compound. The protein expression of VCAM-1 and ICAM-1 can be measured using standard techniques, such as using a cell surface enzyme linked immunosorbent assay (ELISA) or by flow cytometry. Alternatively, VCAM-1 and ICAM-1 mRNA expression can be measured by reverse transcription polymerase chain reaction (RT PCR). See, e.g., Zapolska-Downar et al., *Atherosclerosis* (2001) 155:123-130.

Compounds identified as having MIF-antagonistic activity will be candidates for use as drugs in the treatment of neuropathic pain and addictive behaviors. These compounds can be tested in accepted models of neuropathic pain, such as, but not limited to the tail-flick model (D'Amour et al., *J. Pharmacol. Exp. and Ther.* (1941) 72:74-79); the rat tail immersion model; the carrageenan paw hyperalgesia model; the formalin behavioral response model; the von Frey filament test (Chaplan et al., *J. Neurosci. Methods* (1994) 53:55-63); the chronic constriction injury test (CCI); the Hargreaves test (Hargreaves et al., *Pain* (1998) 32:77-88); and the cold allodynia model (Gogas et al., *Analgesia* (1997) 3:111-118). For a detailed description of these models, see, e.g., U.S. Patent Publication No. 2006/0008446, incorporated herein by reference in its entirety.

Similarly, MIF antagonists can be tested in any of the several known models for addictive behavior, including but not limited to rat models for alcohol and drug addiction (May et al., *J. Pharmacol. Exp. Ther.* (1995) 275:1195-1203); a rat model for amphetamine addiction (Hayne and Wolffgramm, *Psychopharmacol.* (*Berl*) (1998) 140:510-518); a rat model for methadone addiction (Flahery and Sadava, *Arch. Int. Pharmacodyn. Ther.* (1974) 212:103-107; the *C. elegans* model of addiction (Schafer, W. R., *Neuropharmacol.* (2004) 47:123-131); the weaver mutant mouse model of addiction (Maharajan et al., *Prog. Neurobiol.* (2001) 64:269-276); and a model for sugar addiction (Wideman et al., *Nutr. Neurosci.* (2005) 8:269-276).

Agents that have the desired properties are appropriate for further use, for example, in compositions, such as compositions described below.

Formulation Components

Excipients/Carriers

As explained above, ibudilast and/or compounds identified using the screening methods described herein can be provided in pharmaceutical compositions to antagonize MIF activity. Optionally, in addition to the active agent, the compositions may further comprise one or more pharmaceutically acceptable excipients or carriers. Exemplary excipients include, without limitation, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition may also include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A pharmaceutical composition may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition may also contain one or more antioxidants. Antioxidants are used to prevent oxidation, thereby preventing the deterioration of the drug(s) or other components of the preparation. Suitable antioxidants for use in the compositions include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "TWEEN 20" and "TWEEN 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition is selected from the following: at least about 2%, 5%, 10%, 15%, 20%, 25%, 30%, 35%, 40%, 45%, 50%, 55%, 60%, 65% 70%, 75%, 80%, 85%, 90%, or even 95% by weight.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

Other Actives

A formulation (or kit) in accordance with the invention may contain, in addition to ibudilast and/or a MIF antagonist identified as described herein, one or more additional active agents. Preferably, the active agent is one that possesses a mechanism of action different from that of ibudilast and/or the identified MIF antagonist. Such actives include naltrexone, metoclopramide, loperamide, diazepam, clonidine, and paracetemol.

Sustained Delivery Formulations

Preferably, the compositions are formulated in order to improve stability and extend the half-life of ibudilast and/or another MIF antagonist. For example, ibudilast and/or the MIF antagonist may be delivered in sustained-release formulations. Controlled or sustained-release formulations are prepared by incorporating the active agent into a carrier or vehicle such as liposomes, nonresorbable impermeable polymers such as ethylenevinyl acetate copolymers and HYTREL™ (a thermoplastic polyester elastomer) copolymers, swellable polymers such as hydrogels, or resorbable polymers such as collagen and certain polyacids or polyesters such as those used to make resorbable sutures. Additionally, the active agent can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Delivery Forms

The compositions described herein encompass all types of formulations, and in particular, those that are suited for systemic or intrathecal administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include TWEEN 60, SPAN 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the ULTRAVENT™ (Mallinkrodt), and the ACORN II™ (Marquest Medical Products). A composition of the invention may also be delivered using a pressurized, metered dose inhaler (MDI), e.g., the VENTOLIN™ metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations may optionally include other agents conventional in the pharmaceutical arts and particular type of formulation being employed, for example, for oral administration forms, the composition for oral administration may also include additional agents as sweeteners, thickeners or flavoring agents.

The compositions may also be prepared in a form suitable for veterinary applications.

Method of Administration

Methods of delivery of ibudilast-based or other MIF antagonistic therapeutic formulations include systemic and localized delivery, i.e., directly into the central nervous system. Such routes of administration include but are not limited to, oral, intra-arterial, intrathecal, intramuscular, intraperitoneal, intravenous, intranasal, and inhalation routes.

More particularly, a formulation may be administered for therapy by any suitable route, including without limitation, oral, rectal, nasal, topical (including transdermal, aerosol, buccal and sublingual), vaginal, parenteral (including subcutaneous, intramuscular, intravenous and intradermal), intrathecal, and pulmonary. The preferred route will, of course, vary with the condition and age of the recipient, the particular neuralgia-associated syndrome being treated, and the specific combination of drugs employed.

One preferred mode of administration for delivery of ibudilast and/or another MIF antagonist is directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J. Virol.* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

A particularly preferred method for targeting spinal cord glia is by intrathecal delivery, rather than into the cord tissue itself.

Another preferred method for administering the ibudilast-based compositions is by delivery to dorsal root ganglia (DRG) neurons, e.g., by injection into the epidural space with subsequent diffusion to DRG. For example, a composition can be delivered via intrathecal cannulation under conditions where ibudilast is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, the agent can be delivered to many cells over large areas of the CNS. Any convection-enhanced delivery device may be appropriate for delivery of the desired agent. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a composition is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. For a detailed description regarding CED delivery, see U.S. Pat. No. 6,309,634, incorporated herein by reference in its entirety.

A composition, when comprising more than one active agent, may be administered as a single combination composition comprising a combination of a ibudilast and/or the MIF antagonist and at least one additional active agent of interest. In terms of patient compliance and ease of administration, such an approach is preferred, since patients are often adverse to taking multiple pills or dosage forms, often multiple times daily, over the duration of treatment. Alternatively, albeit less preferably, the combination of the invention is administered as separate dosage forms. In instances in which the drugs comprising the therapeutic composition are administered as separate dosage forms and co-administration is required, the desired agent and each of the additional active agents may be administered simultaneously, sequentially in any order, or separately.

Kits

Also provided herein is a kit containing at least one combination composition of the invention, accompanied by instructions for use.

For example, in instances in which each of the drugs themselves are administered as individual or separate dosage forms, the kit comprises ibudilast and/or another MIF antagonist in addition to each of the drugs making up the composition of the invention, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and naltrexone, the kit may be organized by any appropriate time period, such as by day. As an example, for Day 1, a representative kit may comprise unit dosages of each of ibudilast and naltrexone. If each of the drugs is to be administered twice daily, then the kit may contain, corresponding to Day 1, two rows of unit dosage forms of each of ibudilast and naltrexone, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or another MIF antagonist will range from a total daily dosage of about 0.1 and 200 mg/day, more preferably, in an amount between 0.1 and 100 mg/day, 0.1-60 mg/day, 0.1 and 40 mg/day, or 0.1 and 10 mg/day. Administration can be one to three times daily for a time course of one day to several days, weeks, months, and even years, and may even be for the life of the patient.

Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Efficacy of Ibudilast in Antagonizing MIF Activity

In order to determine whether ibudilast antagonized MIF activity, a peripheral blood mononuclear cell (PBMC) culture model was used. Human PBMCs were isolated by Ficoll gradient. Cells were plated in a 96-well tissue culture plate in RPMI medium without serum and incubated overnight to achieve quiescence. They were then treated with 0.1% DMSO (vehicle) or ibudilast at 10 µM, one hour prior to stimulation with recombinant human MIF (0.8, 8, or 80 nM) or LPS (10 ng/mL). 9 hours post-stimulation, the adherent cells were fixed and analyzed for expression of intracellular adhesion molecule-1 (ICAM-1) and vascular cell adhesion molecule-1 (VCAM-1) via cell surface enzyme linked immunosorbent assay (ELISA).

The results observed (Table 1) indicate that ibudilast antagonizes the recombinant MIF-induced expression of adhesion molecules ICAM-1 and VCAM-1. Importantly, the ibudilast inhibition of the adhesion molecules appeared to be specific to MIF, as LPS induction of adhesion molecules was not significantly affected by ibudilast.

TABLE 1

Effect of 10 μM ibudilast on rMIF-induced cell surface ICAM-1 or VCAM-1 expression in PBMCs

| | % change in ICAM-1 expression | | | % change in VCAM-1 expression | |
|---|---|---|---|---|---|
| Stimulant | without ibudilast | with ibudilast | Stimulant | without ibudilast | with ibudilast |
| MIF 80 nM | 38.8 | −1.3 | MIF 80 nM | 54.9 | 5.4 |
| MIF 8 nM | 4.1 | −0.95 | MIF 8 nM | 26 | 4.4 |
| MIF 0.8 nM | 16.1 | −2.5 | MIF 0.8 nM | 13.2 | −2.9 |
| No Stimulant | 0 | 30.9 | No Stimulant | 0 | 95.1 |
| Vehicle for ibudilast | −1.60 | | Vehicle for ibudilast | 16.2 | |
| LPS 10 ng/mL | 65.6 | 74.5 | LPS 10 ng/mL | 7.4 | −1.5 |

Values represent mean percent change from n = 2 replicates per condition normalized to no stimulant levels.

ICAM-1 and VCAM-1 are adhesion molecules primarily involved in leukocyte trafficking (Hamann and Syrbe, *Rheumatology* (Oxford) (2000) 39 (7):696-699). Increased expression of these adhesion molecules is correlated with inflammation and autoimmune diseases and antagonists may have clinical benefit (Yusuf-Makagiansar et al., *Med. Res. Rev.* (2002) 22 (2):146-167). Expression of ICAM-1 and VCAM-1 is elevated in diabetes-related neuropathy (Jude et al., *Diabetologia* (1998) 41 (3):330-336), and rheumatoid arthritis-related peripheral neuropathy (El et al., *J. Rheumatol.* (2002) 29 (1):57-61. ICAM-1 is implicated in the process of neuro-degeneration in Alzheimer's disease (Pola et al., *Neurobiol. Aging* (2003) 24 (2):385-387), indicating that adhesion molecules play a role in neurological disorders. Thus antagonism of these adhesion molecules may have clinical benefit in inflammatory and neurological disorders.

Potential regulation of ICAM-1 and VCAM-1 by ibudilast in quiescent cells is of uncertain consequence in human neuropathic pain. It may not be relevant to ibudilast's attenuation of neuropathic pain or other neurological disorders as those syndromes may present partly as a result of factor (e.g. MIF) activation of inflammatory cells (e.g. glia, monocytes). Hence, the dominant outcome of therapeutic administration of ibudilast in disorders of glial (or monocyte) activation would likely be reduced adhesion molecule expression and related inflammatory effects.

In summary, the results indicate that ibudilast antagonizes MIF activity by abrogating recombinant MIF-induced expression of adhesion molecules ICAM-1 and VCAM-1. Ibudilast may exert its pharmacological effects including its anti-inflammatory activity and the ability to attenuate neuropathic pain through antagonism of MIF.

Thus, methods for identifying agents for treating neuropathic pain and addiction are described. Also described are methods for utilizing ibudilast for antagonizing MIF activity. Although preferred embodiments of the subject invention have been described in some detail, it is understood that obvious variations can be made without departing from the spirit and the scope of the invention as defined herein.

What is claimed is:

1. A method of selecting a compound that modulates MIF-induced expression of ICAM-1 and/or VCAM-1, said method comprising:
    (a) exposing a peripheral blood mononuclear (PBMC) cell culture to a putative compound that modulates MIF-induced expression of ICAM-1 or VCAM-1;
    (b) providing macrophage migration inhibitory factor (MIF) to said exposed cells in an amount and under conditions that normally provide for expression of intracellular adhesion molecule-1 (ICAM-1) and/or vascular cell adhesion molecule-1 (VCAM-1);
    (c) comparing expression of ICAM-1 and/or VCAM-1 by the cells in (b), to expression of ICAM-1 and/or VCAM-1 in a PBMC cell culture treated with MIF as in (b) in the absence of the putative compound; and
    (d) selecting a compound from (c) that inhibits expression of ICAM-1 and/or VCAM-1 relative to expression of ICAM-1 and/or VCAM-1 in the absence of the compound.

* * * * *